United States Patent [19]
Fuhr et al.

[11] Patent Number: 6,113,768
[45] Date of Patent: *Sep. 5, 2000

[54] ULTRAMINIATURIZED SURFACE STRUCTURE WITH CONTROLLABLE ADHESION

[75] Inventors: Günter Fuhr; Andreas Voigt; Torsten Müller; Rolf Hagedorn, all of Berlin; Bernd Wagner, Looft; Thomas Lisec, Berlin, all of Germany

[73] Assignee: Fraunhofer-Gesellschaft zur Forderung der angewandten Forschung e.V., Munich, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/666,480
[22] PCT Filed: Dec. 23, 1994
[86] PCT No.: PCT/DE94/01530
§ 371 Date: Sep. 9, 1996
§ 102(e) Date: Sep. 9, 1996
[87] PCT Pub. No.: WO95/17258
PCT Pub. Date: Jun. 29, 1995

[30] Foreign Application Priority Data

Dec. 23, 1993 [DE] Germany ............................ 43 44 351
Jan. 14, 1994 [DE] Germany ............................ 44 00 955

[51] Int. Cl.⁷ .................... G01N 27/26; G01N 27/447
[52] U.S. Cl. .................... 204/643; 204/450; 204/547; 204/600
[58] Field of Search .................... 204/450, 547, 204/600, 643

[56] References Cited

U.S. PATENT DOCUMENTS

| | | |
|---|---|---|
| 3,908,263 | 9/1975 | Matarese .................................. 29/592 |
| 4,390,403 | 6/1983 | Batchelder .............................. 204/547 |
| 5,126,022 | 6/1992 | Seane et al. . | 
| 5,308,542 | 5/1994 | Poetsch .............................. 252/299.63 |
| 5,344,535 | 9/1994 | Betts et al. . |
| 5,454,472 | 10/1995 | Benecke et al. ..................... 209/127.1 |
| 5,569,367 | 10/1996 | Betts et al. . |
| 5,645,702 | 7/1997 | Witt et al. . |
| 5,653,859 | 8/1997 | Parton et al. . |

FOREIGN PATENT DOCUMENTS

| | | | |
|---|---|---|---|
| 2264783 | 9/1993 | United Kingdom | ................... 204/466 |
| WO9111262 | 8/1991 | WIPO . | |
| WO911262 | 8/1991 | WIPO . | |

OTHER PUBLICATIONS

Fuhr et al., Asynchronous Traveling–Wave Induced Linear Motion of Living Cells, Studia Biophysica vol. 140, No Month Available (1991) No. 2, pp. 79–102.

Schnelle, et al., Three–Dimensional electric field traps for manipulation of cells—calculation and experimental verification, Biochem. et Biophysica Acta, 1157 No Month Available (1993) pp. 127–140.

Melcher, Traveling–Wave Induced Electroconvection, The Physics of Fluids, Aug., 1966, vol. 9, No. 8, pp. 1548–1555.

(List continued on next page.)

*Primary Examiner*—Jill Warden
*Assistant Examiner*—John S. Starsiak, Jr.
*Attorney, Agent, or Firm*—Duane, Morris & Heckscher

[57] ABSTRACT

An ultra-miniaturized surface structure with controllable adhesion having extremely miniaturized (in the sub atomic range) planar electrode strips applied to the surface to which high frequency pulse trains may be applied to generate progressive or stationary standing waves. The electrodes in themselves are combined with dielectric insulating materials with controlled bio-compatibility. The type of electric drive, together with the properties of the surface layers that cover the electrodes, determines the adhesion properties of the surface to a large extent regardless of the used base material. Particle movement is gently influenced, so that for the first time it becomes possible to influence particles in highly physiological nutritive solutions.

16 Claims, 5 Drawing Sheets

OTHER PUBLICATIONS

Fuhr, et al., Microfabricated Electrohydrodynamic (EHD) Pumps for Liquids of Higher Conductivity Journal of Microelectromechanical Sys., vol. 1 No. 3, Sep. 1992, pp. 141–146.

Hagedorn, et al., Traveling–Wave Dielectrophoresis of microparticles, Electrophoresis, 13, 1992, Jan./Feb., No. 1/2 pp. 49–54.

Huang, et al., Electrokinetic behaviour of colloidal particles in traveling electric fields: studies using yeast cells, Journal of Physics D: Applied Physics 26(1993) Sep. 14, No. 9, pp. 1528–1535.

Adamson, et al., Conference Record of the 1986 IEEE Industry Applications Society Annual Meeting Part II, Sep. 28—Oct. 3, p. 1350.

Fuhr, G., et al., Pumping of Water Solutions in Microfabricated Electrohydrodynamic Systems, Micro. Electro. Mechanical Sys. '92, Feb. 4–7, 1992.

Fuhr, G., et al. Linear Motion of Dielectric Particles and Living Cells in Microfabricated Structures Induced by Traveling Electric Fields, Proceedings, IEEE MEMS—Micro Electro Mechanical Sys., Japan, Nara, pp. 259–264, Jan. 1991.

Masuda, et al., Movement of Blood Cells in Liquid by Nonuniform Traveling Field, IEEE Transactions on Industry Applications, vol. 24, No. 2, Mar./Apr. 1988, pp. 217–222.

Masuda, et al., Industry Applications Society, IEEE–IAS 1985 No Month Available Annual Meeting, pp. 18–1423.

Müller, et al., A traveling–wave micropump for aqueous solutions: Comparison of 1 g and $\mu$g results, Electrophoresis No Month Available 1993, 14, pp. 764–772.

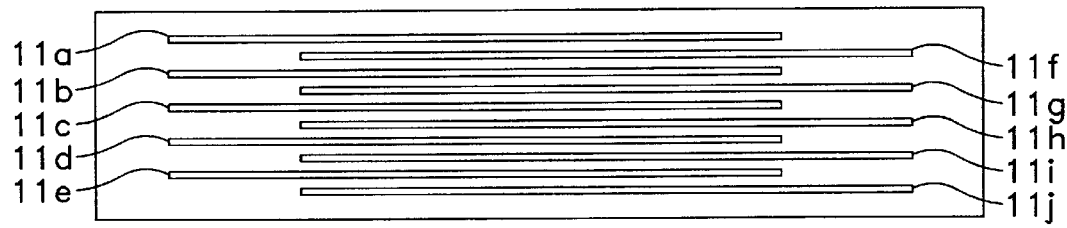
FIG. 1a
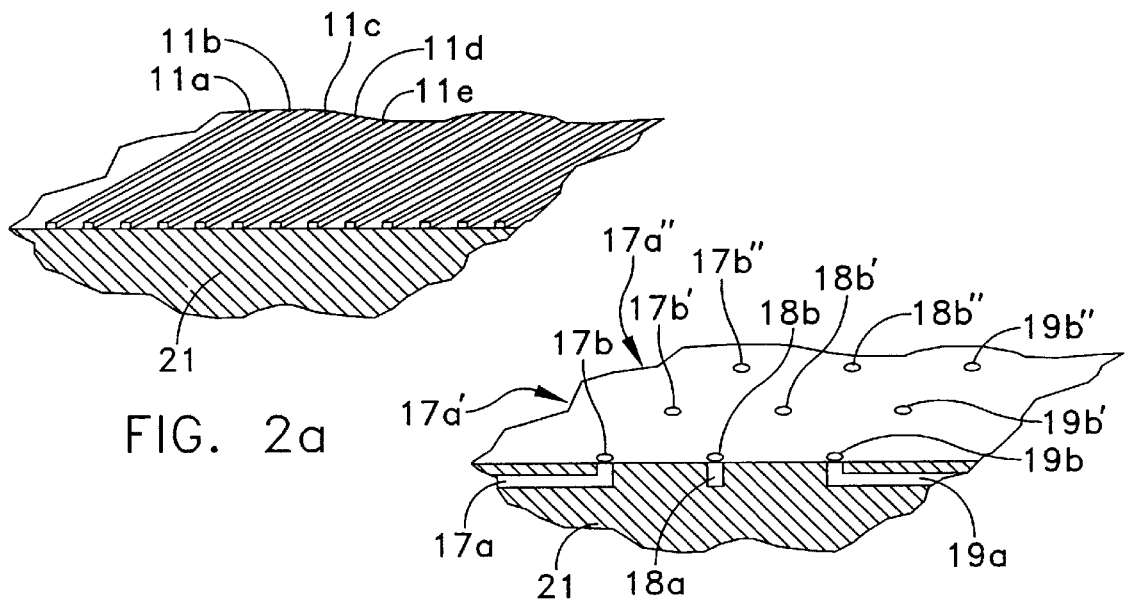
FIG. 2a
FIG. 2b
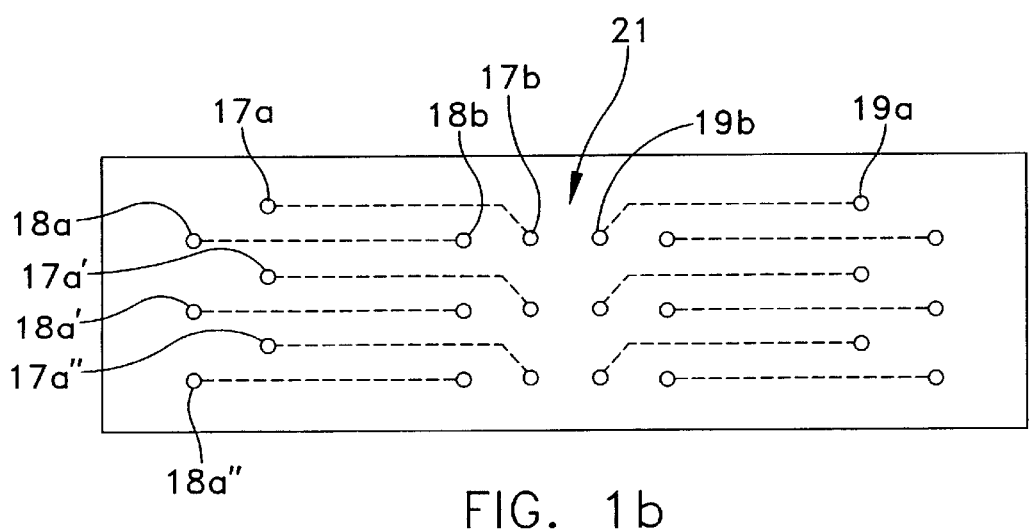
FIG. 1b

ULTRAMINIATURIZED SURFACE STRUCTURE WITH CONTROLLABLE ADHESION

BACKGROUND OF THE INVENTION

1. Field of the Invention

The invention relates to a conductive surface structure for influencing suspended microscopic particles and cells. It also relates to the use of said structure for controlling the adhesion of the particles and cells.

2. Prior Art

In medical technology, biocompatibility research, especially in the production of transplantable materials but also in biological-pharmacological research for a long time, surfaces have been sought with repelling effects on particles and cells in physiological and technical solutions on the one hand but which in certain cases promote adhesion (BOGRAND, P. (ed.), Physical Basis of Cell-Cell-Adhesion, CRC Press, Inc., Boca Raton, Fla., 1988. CURTIS, A. S. G., PITTS, J. D. (eds.), Cell Adhesion and Motility, Cambridge University Press, Cambridge, 1980. GRINELL, F., Int. Rev. Cytol, 53:65–144, 1978. LEE, L. H., Recent Advances in Adhesion, Gordon & Breach, London, 1973. OTTEWILL, R. H., ROCHESTER, C. H., SMITH, A. L. (eds.), Adsorption from Solution, Academic Press, London. PERELSON, A. S., DeLISI, Ch., WIEGEL, F. W., Cell Surface Dynamics, Concepts and Models, Marcel Dekker, Inc., New York, Basel, 1984). As a rule this "surface modification" is achieved by hydrophilization or hydrophobization, via the attachment of charged molecular groups or by local attachment of highly specific bonding sites (e.g., antibodies). The disadvantage of these surface modifications is their small reach in the particle suspension (generally a few Å), the extremely variable long term stability and the absence of controllability of the effect.

The fact that electrical fields can be decoupled via electrodes in a particle or cell suspension and, by polarization of the particles, molecules and cells can be forced away from or toward the electrodes was investigated in detail by POHL in 1978 (POHL, H. P., Dielectrophoresis, Cambridge Press, Cambridge 1978) and established in patents such as U.S. Pat. No. 4,390,403.

These forces which are called dielectrophoresis may have both attracting (positive dielectrophoresis) and repelling (negative dielectrophoresis) effects. The phenomenon is utilized not only for the collection of dirt particles in macroscopic filters but also for the collection and separation of cells and microparticles in microstructures, to be sure until now only with limitations for the following reason:

(i) Electrodes were used in the macroscopic range and, miniaturized down to a few micrometers, and also were generated on planar surfaces. The high frequency electrical fields decoupled in the liquid then penetrate with almost the same field intensity through the entire cell resulting in a high stress on the objects (cells and particles), and very high excitation voltages are necessary (a few V up to a few 100 V).

(ii) The electrodes are still so large that cells can be deposited on them although the field is switched on, since they no longer detect neighboring electrodes on the wider electrodes so that the sought effect that is is nullified. This problem arises, for instance, in WO 91/11262 (P & B Sciences Ltd.) where an electrode array is utilized which may have a chamber shape (cf. FIG. 1B there) but its size and dimensions are not adapted to the particles influenced. This Publication rather deals broadly with the sizes and shapes of "nonuniform magnetic fields" and their effect on chemical reactions between the cells.

(iii) Cells or particles coming into contact with electrodes or directly attracted by them are changed irreversibly because of the metal/cell surface reaction.

High frequency traveling waves generated by electrical signals were utilized by MELCHER for pumping oils (MELCHER, J. R., The physics of fluids, 9:1548–1555, 1966). Toward the end of the 1980's and in the early 1990's this principle could also be realized in microchannels by means of electrode structures prepared by semiconductor technology. The principle is based on stabilization of a temperature gradient and generation of phase shifted space charges. Here also the width of the electrodes was a few 10 $\mu$m (FUHR, G. et al., MEMS 92, Proceedings, 1992).

The fact that particles and cells can be selectively moved by means of traveling electrical fields was demonstrated by MASUDA (MASUDA, S., IEEE Transaction on Industry Applications, 24, 217–222, 1988) and was expanded in 1991 to include high frequency traveling waves (FUHR, G. et al., MEMS 91, Proceedings, 259–264, 1991). The purpose of this planar arrangement was to move individual cells in microchannel systems with the goal of cell separation as explained in more detail in WO 93/3850 (Fraunhofer-Gesellschaft).

SUMMARY OF THE INVENTION

In view of this state of art the present invention has the objective of altering a surface in its adhesion behavior especially for suspended cells and macromolecules in an electrically controllable manner.

This is achieved by the technical idea of an electrically controllable adhesive effect of a subminiature electrode area—especially a dielectrically covered one. The areas must be formed as a strip area or a point area.

The applications of the above mentioned structures according to the invention also includes the formation of bare electrode areas.

By means of a planar surface structured in the subminiature range (below 10 $\mu$m) the microscopic and submicroscopic particles or cells (hereinafter: particles) can be deposited on or repelled from the insulating layer by electrical control without being exposed to high stresses, without changing them chemically and without being confronted with permanent undetachable deposits. The electrode areas acquire a new property by virtue of their dimensions. The electrodes may be dielectrically coated or bare. If they are bare, the strip-shaped or punctiform electrodes may be supplied with much lower voltages in order to keep losses small. Higher voltages (in the volt range) are permitted by the dielectrically coated electrodes. In the subminiature range thus locally strong fields can be generated without burdening the cells with the forces in their full scope. The dimensions of electrodes permit the asymmetrical (unilateral) charging of the cells, because their size is above the subminiature range.

With the electrode systems of the invention one can work with physiological (conductive) and even highly conductive solutions. The circumstance adds to the medical and biological applications of electrical field techniques an area of application which was previously considered to be nonfunctional.

The invention is based on the discovery of applying extremely narrow electrode strips or buttons in recurring sequence to a surface (substrate) which are so narrow that in the most favorable case several electrode paths or a fields of points lying close together correspond to the typical diameter of the particle.

The term subminiature range as used according to the invention refers to a range which begins at about 10 $\mu$m and has no lower limit, although presently it is confined to the ranges around 100 nm to 500 nm by the available production techniques. Experiments have also shown that the effects according to the patent are manifested more clearly when the dimensions are reduced further. Accordingly the range below 1 $\mu$m is especially relevant.

Direct contact of the particles with the electrodes is prevented by a deposited dielectric film, especially a biocompatible film whose material properties are selected such that an electrical field with a just sufficient field intensity can be balanced out in the liquid space near the surface. Since the field intensity increases with the reciprocal distance of the electrodes and is proportional to the applied voltage difference, the possibility of generating the necessary field intensity gradients on one side of the particles and cells arises only in the selected submicrometer range, with low amplitude (100 mV to 1 V).

The field intensity gradients excited in the liquid will drop more rapidly with distance from the surface as the electrodes become narrower, since the parts in the liquid region far from the surface, overlap and neutralize each other. This circumstance greatly reduces the electrical and thermal stress on the particles.

According to the invention this effect can be intensified by applying traveling electrical surface waves, chiefly in the high frequency range (kHz-MHz) so that under the above described boundary conditions an electrical modulation of the adhesion properties of the surface can be performed and the particles will pass into the range of electrical influence of the surface only when they come very close to the surface. The films applied according to the invention on the one hand balance out the traveling electrical field suitably in the near-surface liquid space and on the other prevent electrolytic processes so that they can be used in physiological solutions of high conductivity.

The insulating films are those films which and accordingly insulate the aqueous or conductor solution with particles suspended in it from the electrodes, accordingly "insulates [sic]". This insulation is both mechanical and electrical; a combination of the two above-mentioned possibilities of insulation may also exist. A high dielectric coefficient is favorable but is not absolutely necessary.

BRIEF DESCRIPTION OF THE DRAWINGS

Preferred examples of embodiment of the invention are explained in the following with reference to the figures.

FIG. 2 and FIG. 4 are sectional views of the structures shown in FIG. 1 and FIG. 3.

FIGS. 1a and 1b are views of a microstructured surface with electrically conducting electrode strips 11 (11a through 11k) or 17b, 18b, 19b without deposited insulating films.

FIGS. 2a and 2b show the corresponding perspective sectional views of the structures shown in FIGS. 1a and 1b on the one hand with strip electrodes lying on them 11a, 11b, . . . and on the other with point electrodes 17b, 17b', 17b'' and feed lines 17a, 18a, 19a embedded in the substrate.

DETAILED DESCRIPTION OF THE PREFERRED EMBODIMENTS

Figure 1:
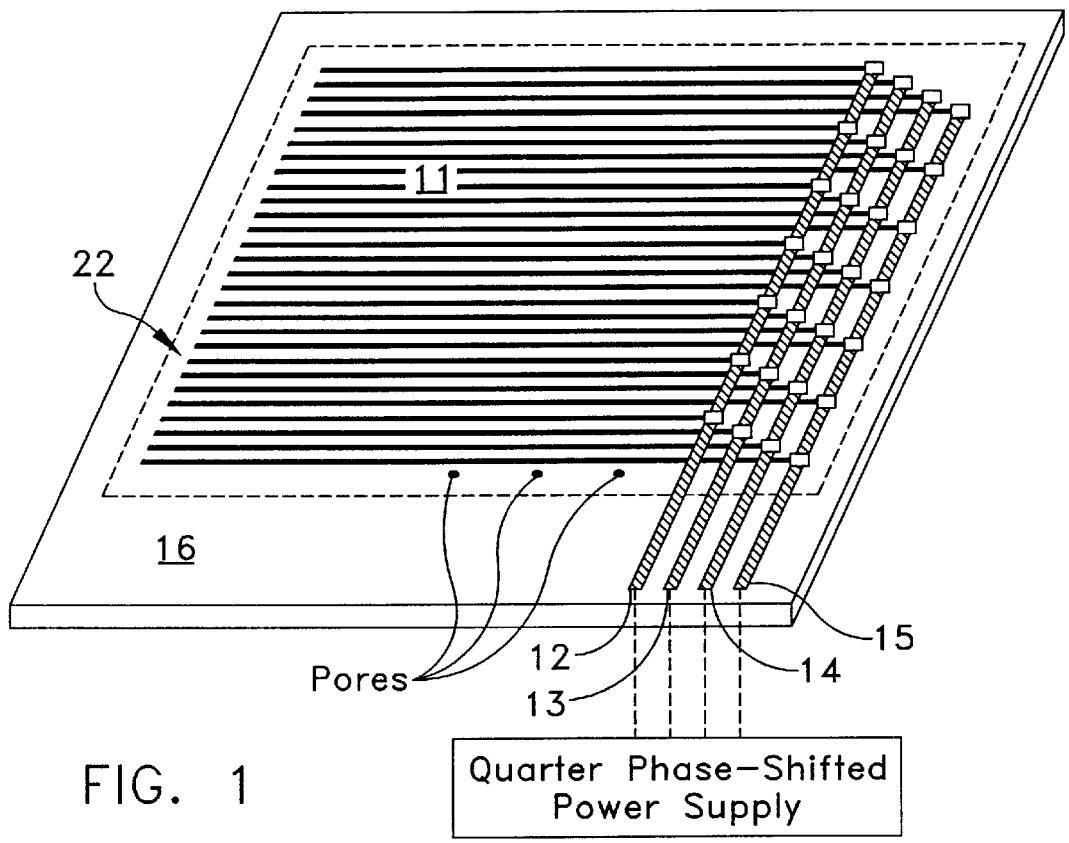
FIG. 1 and FIG. 2 in each case show perspective views of the microstructured surface with electrically conducting electrode strips 22, 42, 44 and deposited insulating films 23, 45, 43.
Figure 2:
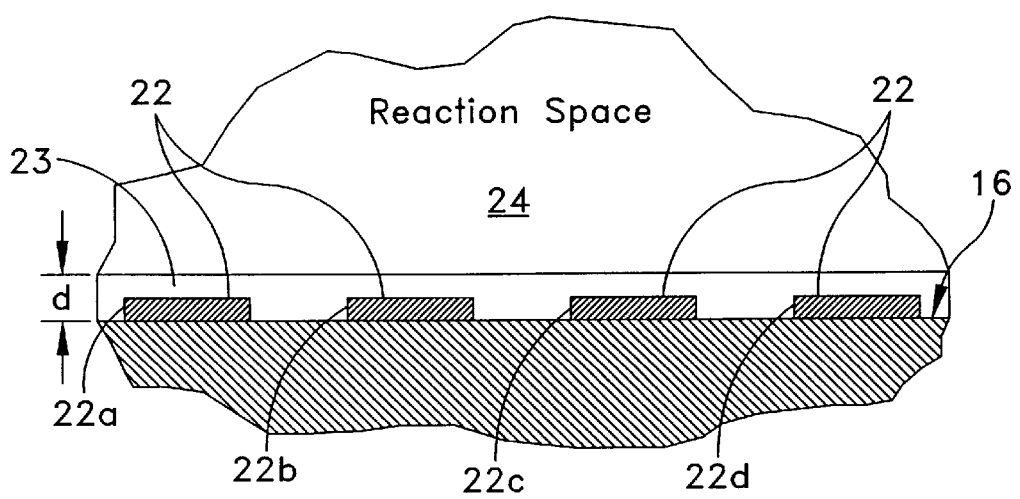

FIGS. 1 and 2 show a planar surface with electrically controllable adhesion behavior (with respect to particles in suspension) with an electrode strip surface 11. The electrodes 22 are connected by 4 power lines 12, 13, 14 and 15 into groups of 4 electrodes each and can be modulated periodically in this group configuration (a, b, c, d . . . ). In the same way groups of 3 or even more electrodes can be formed. In this way it is possible to generate electrical traveling waves which can be fixed in their direction.

In the example given this is achieved by applying four periodic signals in each case one quarter phase-shifted to the power lines 12, 13, 14, and 15 so that a traveling field is generated developing with a preassignable speed via the electrode strip surface 11 which gently moves the particles in the suspension.

The insulating film or layer 23 applied to the electrodes balances out the traveling fields dielectrically in the liquid 24 above them and may be biocompatible.

Surface waves are balanced out the more strongly the higher the relative dielectric constants and the thinner the insulating film 23 are selected to be. Typical thicknesses for the applications described are a few 10 nm up to a few micrometers (submicrometer range). The applied film however may also be replaced or complemented by monomolecular, bimolecular and multimolecular films. With these films the cell-specific biocompatible properties can be substantially supported. Polyurethane, Teflon, metal and semiconductor oxides or insulators ($SiO_2$, SiC, $Si_3N_4$) come into consideration as materials. The molecular films may be lipids, detergents, polymers or the like.

Via these insulating films 23 the surfaces may additionally be structured and predetermined laterally in their adhesion properties.

The adhesion properties are controlled by imposing frequency, mutual phase relationships and amplitude on the high frequency signals. In the example the electrical surface layers in each case are traveling in one direction. By changing the wiring via the power lines 12, 13, 14, and 15, opposing, standing, and alternating waves can be achieved. The thus modulated unit may be applied to solid or flexible substrates 21 (with the surface 16) so as to macroscopically cover the surface.

These structures may also form the walls of hoses or reaction spaces (treatment cells) in rolled-up form.

The structures described are produced by known production techniques of semiconductor technology, e.g., in electron beam lithography and known deposition and etching procedures.

Figure 3:
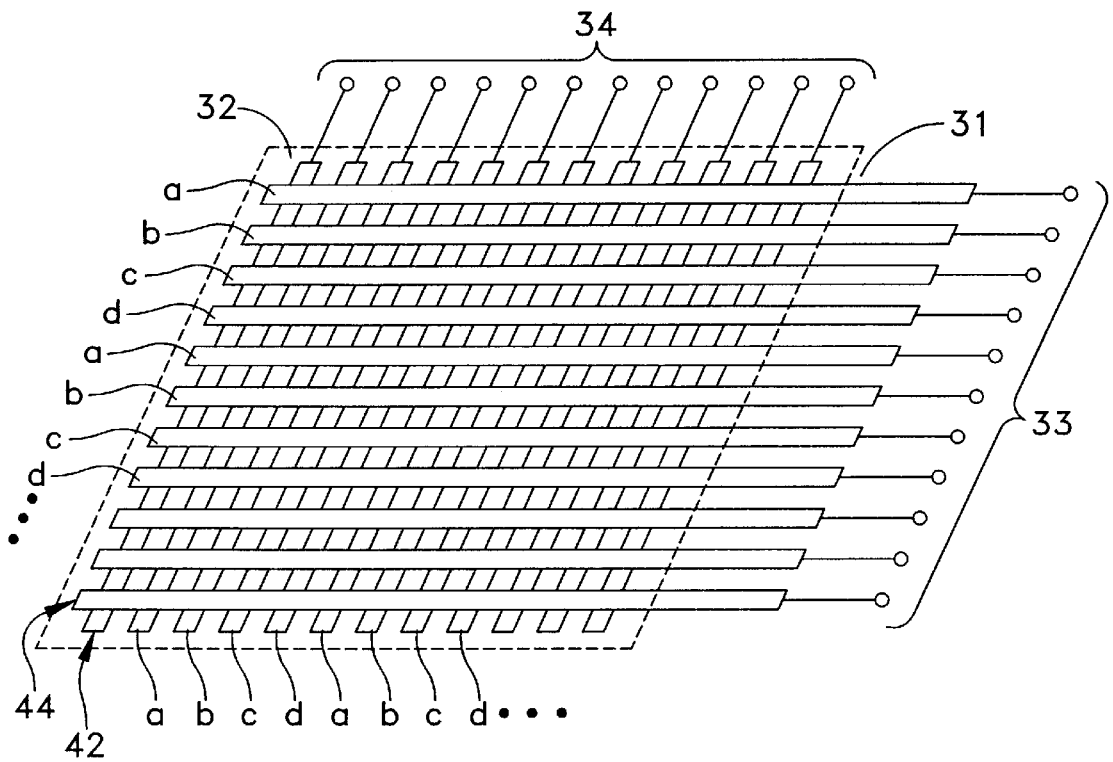
Figure 4:
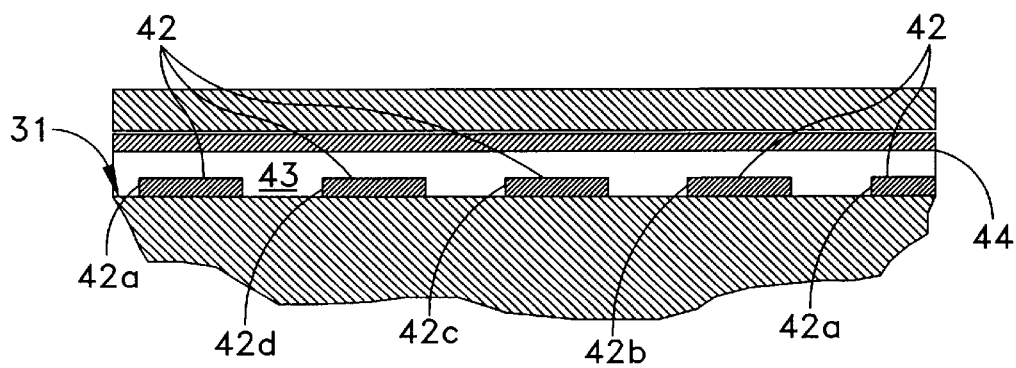

FIGS. 3 and 4 show the surface structure in which two electrode strip surfaces 42, 44, dielectrically insulated against each other are arranged rotated by 90°. All electrode strips are passivated with insulating cover layers 31, 32 (FIG. 3) and 43, 45 (in section in FIG. 4) through which the traveling surface waves of both electrode planes can be balanced out in the liquid. Depending on application purpose the individual electrodes can be combined into groups and connected to each other or be hooked up individually. The connection is accomplished by a feed line 33, 34 which leads to the electrode strips or groups.

The contour of strip electrodes (FIGS. 1, 1a, 1b) need not be straight but may lie in a curved, zigzagged, meandering or spiral form on the surface 41. In this way in addition to the adhesion properties, particles located above the electrode area can be collected and deposited at certain locations on the surface array or be removed from them. Samples can be produced in a controlled way.

FIGS. 1a and 2a show a surface which can be governed electrically in adhesion behavior (with respect to particles in suspension) with an electrode strip surface 11a, 11b, 11c (11), which is not covered by a dielectric film. Therefore bare electrodes are involved. The voltage that can be applied to them is of the lower volt range—the smaller the strip width and the strip spacing, the lower also the voltage.

FIGS. 1b and 2b show a surface which is electrically controllable in adhesion behavior (relative to particles in suspension) with electrode points 17b, 17b', 17b'', 18b, 18b', 18b'' and 19b, 19b' and 19b''. The "electrode buttons" are not coated by dielectric film. The mutual spacing is in the range of 100 nm to 1 $\mu$m. The voltages applied to them are in the range measured above for FIG. 1a. The feed lines to the electrode points are embedded in the substrate 21. Therefore the feed lines 17a, 17a', 17a'', 18a . . . and 19a . . . are insulated from the suspension; electrical losses may be avoided.

Figure 5:
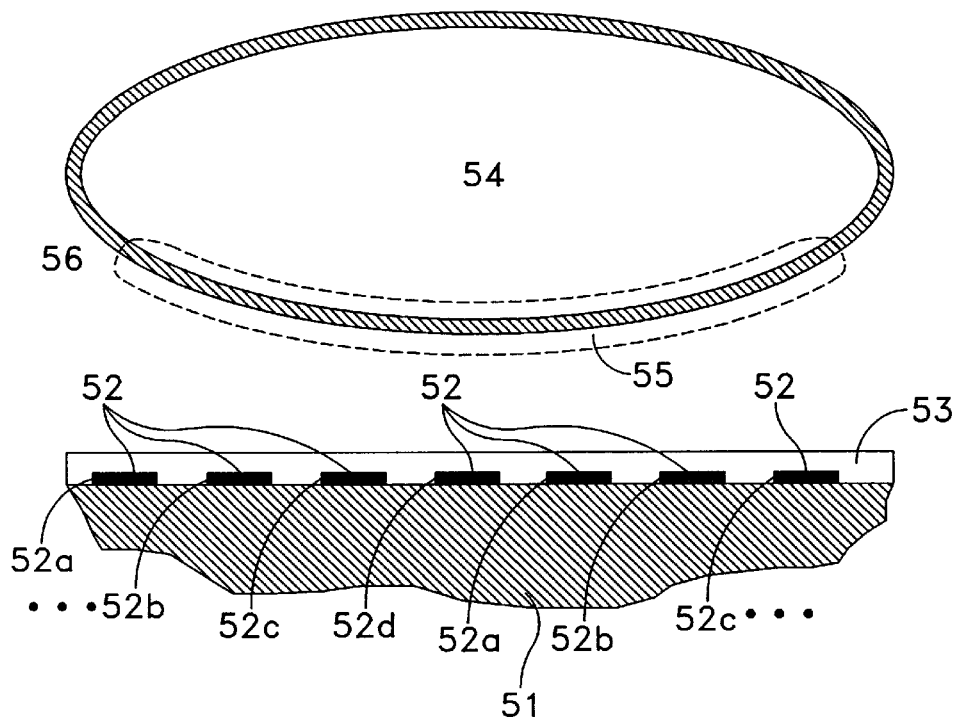
FIG. 5 serves to explain the asymmetrical force acting on a cellular object 54 whose dimension is greater than the structure of the electrodes.

FIG. 5 shows the schematic size ratios such as occur during the use of animal cell suspensions 56 with cell sizes 54 of a few micrometers and represent the most favorable case for physiologically strongly conductive cell suspensions. It is obvious that the submicrometer-wide electrodes 52 limit the influence of the surface structures described on the space 55 near the surface. As a result the cell and particle adhesion behavior can be influenced without stress.

It is assumed that the surface traveling wave influence in solution extends only 2 to 5 electrode widths. This defines a degree of structuring which varies with particles size.

Each of the examples of embodiment shown can be varied geometrically and incorporated in hybrid structures. The surface structure according to the invention may also be used to keep free of trace elements that are used as sensors.

Figure 6:
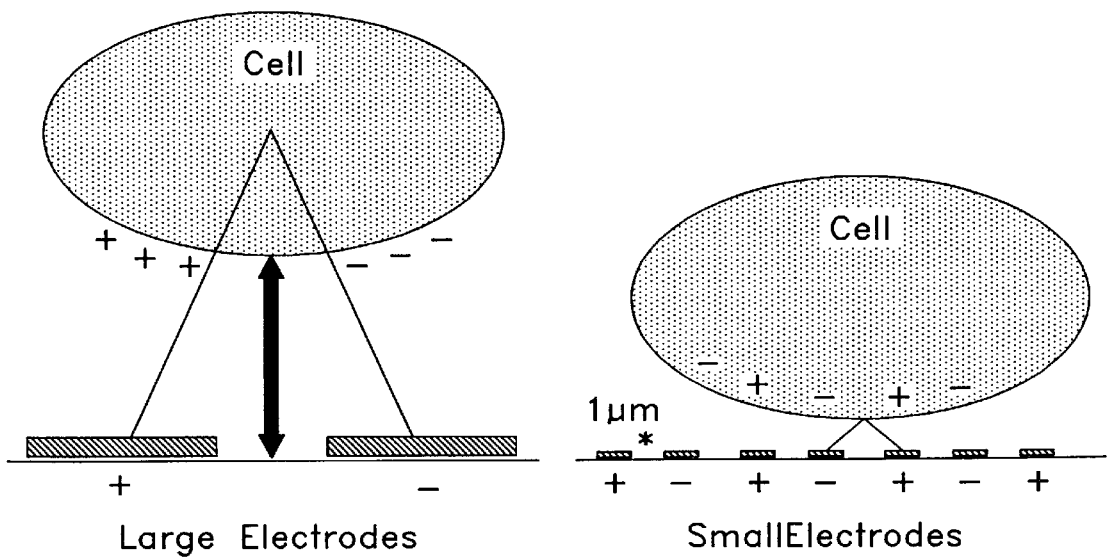
FIG. 6 illustrates in two figures the cell-sparing effect of surface structures in the 1 $\mu$m range.

FIG. 6 illustrates the effect obtained with the above-described subminiature structures with respect to a cell of the order of a few tens of micrometers in size. While large electrodes having a spacing from center to center on the order of 30 $\mu$m stress the cells strongly over a large area with positive and negative influence charges so that considerable potential gradient arises in the cell, this will no longer happen with the subminiature electrodes shown in the right half of the figure, because here the variable charges recur on the surface of the cell with a period which corresponds approximately to the period of the subminiature electrode strips so that only a slight potential gradient arises and a uniformly alternating voltage gradient builds up on the surface of the cell. This is especially sparing for the cell and stresses it only slightly while the force applied by the narrow electrode strips on the cell is still considerable.

With this effect and the structures shown in FIGS. 1, 3 and 5, protective field force shields are achieved in a limited region above the subminiature electrode structure.

An example of dimensions and materials with which FIG. 5 was implemented, for example, is the following:

Gold electrode strips 52 have a width of 500 nm. The gaps between the electrodes strips 52a, 52b, 52c, 52d . . . in each case amount to 500 nm. The electrode height—deviating from the rectangular structure on FIG. 5—is about 500 nm. The electrode strip structure was generated by electron beam lithography. The substrate 51 is silicon. The covering film 53 is of glass. Also of glass is the intermediate space in each case between two electrode strips (see, e.g., FIG. 4). The field used (the applied voltage) has a frequency of 1 MHz and a voltage of 1.5$V_{pp}$. The erythrocyte suspension used has a conductivity of 1.2 S/m. Even after more than 1 hour the surface structure of the example described remained without any deposition of the erythrocytes.

The example and the presentation of the various subminiature structures points to the possibility that biocompatible surfaces can be created with which the deposition of particles can be prevented so that thromboses can be avoided. Besides this, the possibility arises of using sensory systems with which the deposition of particles on the sensor surfaces can be prevented, thus creating sensors having a high service life.

Other applications of the structures described are in implantation techniques and the structure of optics.

Implantation techniques are generally known to include implant objects which are implanted into living bodies. Such implanting objects are not shown, but generally have surfaces which can be covered by the surface structures described herein, to make them biocompatible, preventing deposition of particles and therefore thromboses.

Figure 7B:
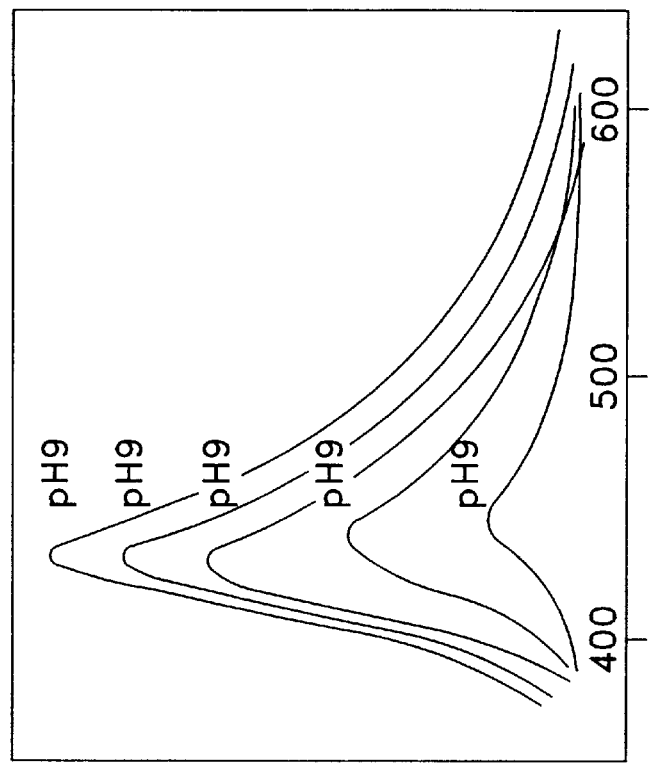
FIGS. 7a and 7b are representations of how acid and base (also anode and cathode) can be generated with potential-modulated electrodes in order to stabilize the pH gradient of FIG. 7b in the $\mu$m range.
Figure 7A:
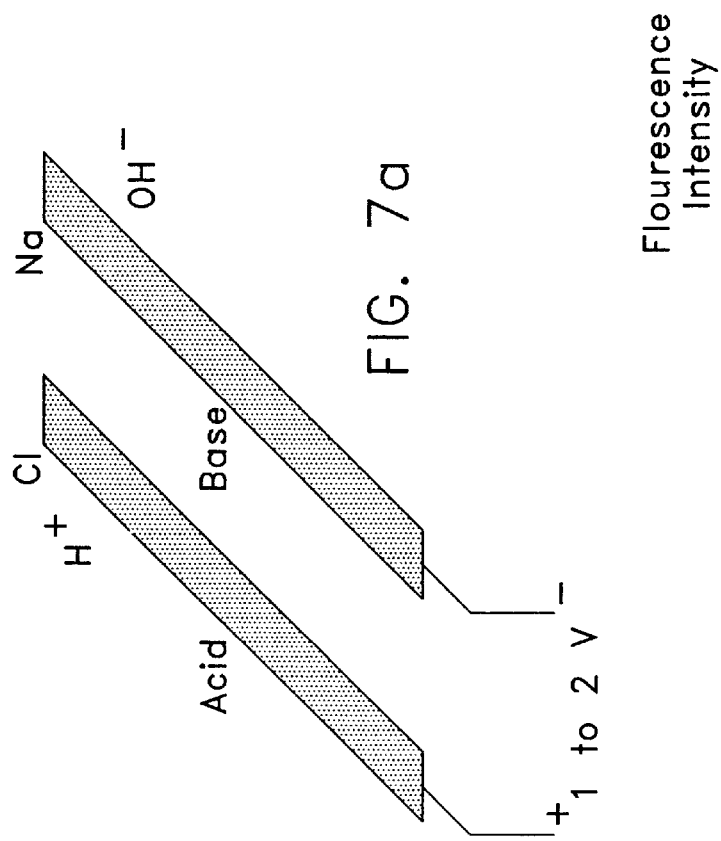

The possibility of application of the pH gradient stabilized in the $\mu$m range explained in FIGS. 7a and 7b should not go without mention. With this the possibility exists of visualizing electrode defects; chemical micro-reaction systems can be built up; pharmacological test systems can be created and finally biological/medical cell cultures can be studied with it.

The electrode structure in FIG. 7a permits the potential-modulation and generation of acid and base, also cathode and anode. This is possible only with electrical control of the electrode structure created in the $\mu$m range. The individual electrodes are pulsed asymmetrically with low voltages in the range between 1 V and 2 V. Depending on the electrode spacing (FIG. 7b) different pH values arise, with which a gradient can be created above the electrode structure. The pH gradient can be made visible via a pH dependent fluorescence marker.

What is claimed is:

1. A surface structure having electrodes on a substrate and having a surface for use with one of an aqueous and conductive solution having particles suspended therein, comprising:

a plurality of electrodes each having a first portion having a width and a second portion electronically connected to a power supply for providing phase shifted high frequency periodic signals, said electrodes being spaced apart by less than one $\mu$m and being arranged in groups for controlling an adhesion behavior of said surface structure in a direction substantially perpendicular to the surface.

2. A surface structure in accordance with claim 1, wherein each of said groups has at least three electrodes for providing traveling electrical surface waves from the high frequency periodic signals applied by the power supply, said waves having directions of travel, said directions being one of periodically changing, directed toward one another and directed away from one another.

3. A surface structure in accordance with claim 2, wherein the power supply is coupled to the electrodes in each said group, wherein each of the groups of electrodes is controlled with high frequency periodic signals different in frequency for providing traveling electrical surface waves having different traveling speeds.

4. A surface structure in accordance with claim 1, further comprising an insulating film covering at least the first portion of the electrodes.

5. A surface structure in accordance with claim 4, wherein the insulating film has at least two layers.

6. A surface structure in accordance with claim 1, wherein said groups include first and second groups of said electrodes that are mutually insulated from one another, and the first groups are arranged above the second groups.

7. A surface structure in accordance with claim 1, wherein the substrate comprises one of silicon, glass, plastic, ceramic and a flexible foil material.

8. A surface structure in accordance with claim 1, in combination with at least a portion of a tube or reaction space, hose, sensory surface and implant surface.

9. A surface structure in accordance with claim 1, further comprising at least one insulating film at least partially covering the electrodes, said insulating film having a thickness of less that one $\mu$m.

10. A surface structure in accordance with claim 1, further comprising an insulating film covering at least the first portion of the electrodes, said insulating film comprising one of $SiO_2$, SiC, $Si_3N_4$, barium titanate, tantalum oxide and a masking lacquer.

11. A surface structure in accordance with claim 1, wherein the width and spacing of said electrodes is substantially below one $\mu$m.

12. A surface structure in accordance with claim 11, wherein the width and spacing of said electrodes is below 500 nanometers.

13. A surface structure in accordance with claim 1, further comprising an insulating film for covering at least the first portions of the electrodes, said insulating film being one of a mechanical separating layer, an electrical insulating layer and a combination thereof.

14. A surface structure in accordance with claim 1 further comprising feed lines to the electrodes, wherein said feed lines are embedded in said substrate and adapted for coupling to the power supply and to said second portions of the electrodes, said first portions of said electrodes being uncovered for direct connection to the solution.

15. A surface structure in accordance with claim 1, further comprising an insulating film for covering at least the first portions of the electrodes, said insulating film being a dielectric film with a substantial dielectric coefficient.

16. A surface structure in accordance with claim 1, further comprising an insulating film for covering at least the first portions of the electrodes, said insulating film being biocompatible.

* * * * *